United States Patent [19]

Hadley

[11] 4,331,816
[45] May 25, 1982

[54] ANILINE ANALEPTICS

[75] Inventor: Michael S. Hadley, Sawbridgeworth, England

[73] Assignee: Beecham Group Limited, England

[21] Appl. No.: 148,778

[22] Filed: May 12, 1980

Related U.S. Application Data

[62] Division of Ser. No. 894,942, Apr. 10, 1978, Pat. No. 4,223,034.

[30] Foreign Application Priority Data

Apr. 22, 1977 [GB] United Kingdom ............... 16765/77

[51] Int. Cl.³ .................. C07C 103/75; C07C 103/82; C07C 125/06
[52] U.S. Cl. ..................................... 564/164; 564/157; 564/165; 560/27; 424/300; 424/324
[58] Field of Search ................ 424/324, 300; 564/164, 564/157, 194, 165; 560/29, 27

[56] References Cited

U.S. PATENT DOCUMENTS 3,647,877 3/1972 Weber et al. ..................... 424/324
4,097,487 6/1978 Murakami et al. .................. 564/168

Primary Examiner—Natalie Trousof
Assistant Examiner—L. Hendriksen
Attorney, Agent, or Firm—Jacobs & Jacobs

[57] ABSTRACT

This invention concerns compounds of the formula:

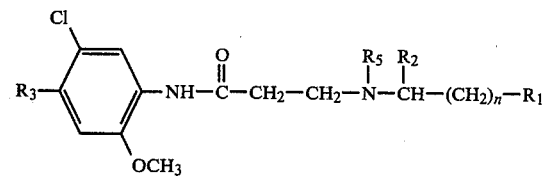

and the N-oxides and the pharmaceutically acceptable salts thereof wherein $R_1$ is phenyl unsubstituted or substituted by fluoro chloro, bromo, alkyl of 1 to 3 carbon atoms or alkoxy of 1 to 3 carbon atoms;

$R_2$ is hydrogen or alkyl of 1 to 4 carbon atoms;

$R_3$ is hydrogen, nitro, amino,

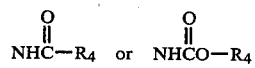

in which $R_4$ is alkyl of 1 to 4 carbon atoms unsubstituted or substituted with up to three chlorine atoms or with three fluorine atoms on the same carbon atoms;

$R_5$ is alkyl of 1 to 4 carbon atoms n has a value of 0, 1 or 2.

25 Claims, No Drawings

ANILINE ANALEPTICS

This application is a division of Ser. No. 894,942, filed Apr. 10, 1978, now U.S. Pat. No. 4,223,034.

The present invention relates to aniline derivatives possessing major tranquillizing activity, to pharmaceutical compositions containing them, to the process for their preparation and to intermediates useful in that process.

Metoclopramide, which is the chloroaniline derivative of the formula (I):

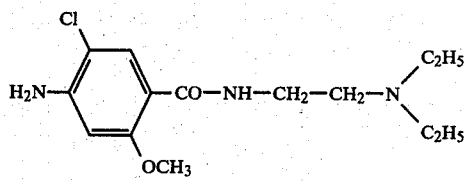

has found widespread clinical use due to its ability to enhance the rate of gastric emptying. A structurally distinct group of chloroaniline derivatives has now been found which possess a different pharmacological activity, namely major tranquillizing activity.

The present invention provides the compounds of the formula (II):

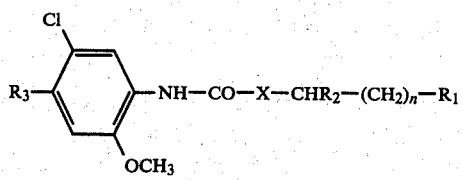

wherein $R_1$ is a phenyl group optionally substituted by a fluorine, chlorine or bromine atom or an alkyl or alkoxyl group of up to 3 carbon atoms; $R_2$ is a hydrogen atom or an alkyl group of up to 4 carbon atoms; $R_3$ is a hydrogen atom or an amino group, a nitro group or a group of the formula $NHCOR_4$ or $NHCO_2R_4$ where $R_4$ is an alkyl group of up to 4 carbon atoms optionally substituted by one, two or three chlorine atoms or by three fluorine atoms attached to the same carbon atom; n is 0, 1 or 2; and X is a group of the sub-formula (a), (b), (c) or (d):

—CH$_2$—CH$_2$—NR$_5$— (a)

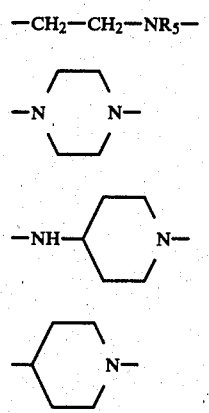

wherein $R_5$ is an alkyl group of up to 4 carbon atoms; or a N-oxide thereof of the nitrogen atom to which the $CHR_2$—$(CH_2)_n$—$R_1$ moiety is attached; or a salt thereof.

Suitably $R_1$ is a phenyl, p-chlorophenyl, p-methylphenyl, p-methoxyphenyl or like group.

Preferably $R_1$ is a phenyl group.

Suitably $R_2$ is a hydrogen atom or a methyl, ethyl, n-propyl or n-butyl group.

More suitably $R_2$ is a hydrogen atom or a methyl group.

Preferably $R_2$ is a hydrogen atom.

Most suitably n is 0.

From the foregoing it will be realised that a favoured $CHR_2$—$(CH_2)_n$—$R_1$ moiety is the benzyl group.

Suitably $R_3$ is a hydrogen atom. Compounds in which $R_3$ is a hydrogen atom are envisaged primarily as intermediates.

Suitably $R_3$ is a nitro group. Compounds in which $R_3$ is a nitro group are envisaged primarily as intermediates.

Suitably $R_3$ is an amino or $NHCOR_4$ group where $R_4$ is an alkyl group of up to 4 carbon atoms. Compounds in which $R_3$ has one of these meanings are envisaged as pharmacologically active compounds and especially when $R_3$ is an amino group.

More suitably $R_3$ is an amino group or alternatively an acetylamino, propionylamino, methoxycarbonylamino, ethoxycarbonylamino or like group.

Most suitably $R_3$ is an amino or acetylamino group.

Preferably $R_3$ is an amino group.

One group of favoured pharmacologically active compounds of the formula (II) is that of the formula (III):

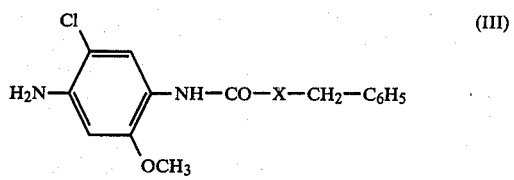

wherein X is as defined in relation to formula (II) and salts thereof.

A further group of favoured pharmacologically active compounds of the formula (II) is that of the formula (IV):

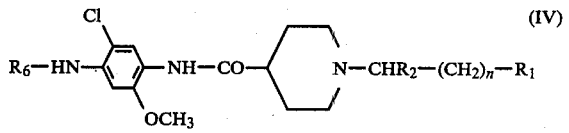

and salts thereof wherein $R_1$, $R_2$, and n are as defined in relation to formula (II) and $R_6$ is a hydrogen atom or a $COR_4$ or $CO_2R_4$ group where $R_4$ is as defined in relation to formula (II).

Particularly suitable values for $R_1$, $R_2$ and n are as described in relation to the compounds of the formula (II).

The compounds of the formula (IV) wherein $CHR_2$—$(CH_2)_n$—$R_1$ represents a benzyl group have especially favourable neuroleptic activity but do not have a high level of disadvantageous side effects on the gastro intestinal system.

Since the compounds of the formula (II) are nitrogenous bases they are able to form acid addition salts in a conventional manner. Most suitably these salts are those formed with pharmaceutically acceptable inorganic or organic acids such as hydrochloric, hydrobromic, orthophosphoric, methanesulphonic, toluenesulphonic, acetic, fumaric, tartaric, lactic, citric, succinic or the like acid. Those compounds of the invention which contain more than one basic nitrogen atom may form di-acid addition salts as well as mono-acid addition salts, for example the dihydrochloride salt as well as the monohydrochloride salt.

The present invention also provides a pharmaceutical composition which comprises a compound of this invention and a pharmaceutically acceptable carrier.

Most suitably the compound used in the composition of this invention will not be one in which $R_3$ is a hydrogen atom or a nitro group. Preferably the compound used in the composition of this invention will be one in which $R_3$ is an amino group.

The composition of this invention will normally and preferably be adapted for oral administration although parenteral compositions are also envisaged as useful.

The compositions of this invention will most suitably be presented as unit dose compositions containing from 1 to 200 mg, more usually from 5 to 100 mg, for example from 10 to 50 mg such as 12.5, 15, 20, 25 or 30 mg. Such compositions will normally be taken from 1 to 6 times daily, for example 2, 3 or 4 times daily so that the total amount of active agent administered is within the range 5 to 400 mg.

Preferred unit dosage forms include tablets, capsules and their equivalents.

Injectable compositions of this invention will normally comprise an acid addition salt of the compound of the invention since the free bases tend to be of disadvantageously low aqueous solubility.

The compositions of this invention may be formulated by conventional methods of blending, filling, compressing and the like.

Suitable carriers for use in this invention include diluents, binders, disintegrants, colouring agents, flavouring agents, preservatives and the like. These agents may be utilized in conventional manner, for example in a manner similar to that already used for other mood modifying agents such as clinically used tranquillizing agents.

The present invention also provides a process for the preparation of the compounds of the formula (II) wherein X is a group of the sub-formula (a) or (d) which process comprises the reaction of the compound of the formula (V):

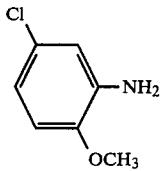

(V)

with a reactive acylating derivative of a compound of the formula (VI):

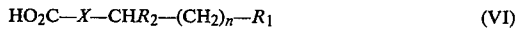

$HO_2C—X—CHR_2—(CH_2)_n—R_1$ (VI)

wherein $R_1$, $R_2$, X and n are as defined in relation to formula (II); thereby producing a compound of the formula (II) wherein $R_3$ is a hydrogen atom; and thereafter if desired nitrating the compound of the formula (II) wherein $R_3$ is a hydrogen atom to yield a compound of the formula (II) wherein $R_3$ is a nitro group; and thereafter if desired reducing the compound of the formula (II) wherein $R_3$ is a nitro group to yield a compound of the formula (II) wherein $R_3$ is an amino group; and thereafter if desired acylating the compound of the formula (II) wherein $R_3$ is an amino group to yield a compound of the formula (II) wherein $R_3$ is a $NHCOR_4$ or $NHCO_2R_4$ group where $R_4$ is defined as in relation to formula (II).

Suitable active acylating derivatives of the acid include acid halides such as the acid chloride, the acid anhydride, mixed anhydrides such as those formed from ethyl chloroformate or equivalent reagents, reactive reagents formed by a carbodiimide such as dicyclohexylcarbodiimide, and esters such as the methyl, ethyl and like esters.

The reaction is normally carried out in non-hydroxylic organic solvent such as tetrahydrofuran, ethyl acetate, toluene, dichloromethane, NN-dimethylformamide and the like. The reaction is normally carried out in the presence of an acid acceptor such as pyridine, triethylamine or the like. The reaction may be carried out at any non-extreme temperature such as $-10°-100°$ C. and more suitably $0°-80°$ C. The higher reaction temperatures are employed with less active derivatives of the acid of the formula (VI) such as esters whereas the lower temperatures are employed with the more reactive derivatives of the acid of the formula (VI) such as mixed anhydrides or the like.

The compound of the formula (II) wherein $R_2$ is hydrogen may be isolated from the reaction mixture in conventional manner, for example by evaporation of the solvents followed, if desired, by chromatography.

The compounds of the formula (II) wherein $R_3$ is a nitro group may be prepared by the nitration of the corresponding compound of the formula (II) wherein $R_3$ is a hydrogen atom.

The reaction may be brought about under reaction conditions known as suitable for the mono-nitration of anisole.

A particularly suitable nitrating agent for use in this process is fuming nitric acid. In general the reagent is added to a solution of the compound of the formula (II) wherein $R_3$ is hydrogen, in solution in an organic solvent such as acetic acid. Normally the reaction is carried out at an ambient or slightly super ambient temperature, for example $15°-45°$ C. and more suitable at about $30°-40°$ C.

The nitro compound may be obtained from the reaction mixture by such conventional means as neutralisation followed by extraction into a water immiscible organic solvent such as ethyl acetate from which it may be recovered by evaporation. If desired the nitro compound may be purified by chromatography or by recrystallisation of the free base or an acid addition salt thereof.

A process provided by this invention for the preparation of the compounds of the formula (II) wherein $R_3$ is an amino group comprises the reduction of a corresponding compound of the formula (II) wherein $R_3$ is a nitro group.

The reduction of the compounds of the formula (II) wherein $R_3$ is a nitro group may be effected with reagents known to be suitable for reducing nitroanisole to aminoanisole. A suitable reagent for this reduction is stannous chloride in hydrochloric acid or in mixtures of hydrochloric and acetic acids.

The desired amino compound may be obtained from the reaction mixture by neutralisation followed by extraction into a water immiscible solvent such as ethyl acetate from which it may be recovered by evaporation of the solvent. The initial crude product may be purified by chromatography or crystallisation or by forming an acid addition salt which may be recrystallised.

Those compounds of the invention wherein $R_3$ is a $NH.CO.R_4$ or $NH.CO_2R_4$ group may be prepared from the corresponding compound of the formula (II) wherein $R_3$ is an amino group by reaction with an acylating derivative of the acid of the formula $HO_2C.R_4$ or $HO_2C.OR_4$. Suitable acylating derivatives are as previously described as suitable acylating derivatives of the acid of the formula (VI) and the reaction may proceed as described for the reaction of the compounds of the formula (V) and (VI).

The invention provides a further process for the preparation of compounds of the formula (II) wherein $R_3$ is other than an amino group and X is a group of the sub-formula (b) or (c), which process comprises the reaction of a compound of the formula (VII):

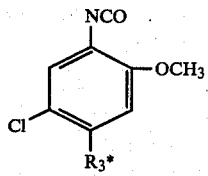

wherein $R_3*$ is a group $R_3$ as defined in relation to formula (II) except an amino group, with a compound of the formula (VIII) or (IX):

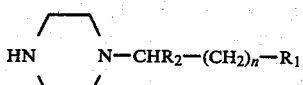

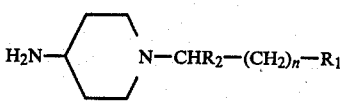

wherein $R_1$, $R_2$ and n are as defined in relation to formula (II).

The reaction may be carried out in an aprotic medium at a non-extreme temperature, for example in toluene at room temperature.

The compound of the formula (VII) may be prepared by heating the corresponding azide, e.g. at 90° in an aprotic solvent such as toluene. The azide may be prepared from the corresponding acid chloride by reaction with sodium azide.

The compounds of the formula (II) wherein $R_3$ is an amino group are able to be converted into mono- or di-acid addition salts by mixing in solution the desired quantity of acid with the base of formula (II). The reaction is generally carried out in a solvent such as in which the starting materials are soluble but in which the resulting salt is insoluble.

This invention also provides a process for the preparation of a compound of the formula (II) wherein $R_3$ is an amino group atom which comprises the deacylation of a corresponding compound of the formula (II) wherein $R_3$ is a group of the formula $NH.CO.R_4$ or $NHCO_2R_4$ wherein $R_4$ is as defined in relation to formula (II).

Generally the hydrolysis reaction may be effected by treatment with a base such as an alkali metal hydroxide in an aqueous alcoholic. The reaction is usually carried out at an ambient or elevated temperature, for example at about 20°–100°, more usually at about 40°–80°.

In a further aspect this invention provides a process for the preparation of a compound of the formula (II) wherein X is a group of the sub-formula (d) which comprises the reduction of a corresponding compound of the formula (X):

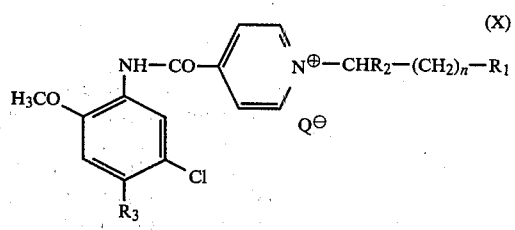

wherein $R_1$, $R_2$, $R_3$ and n are as defined in relation to formula (II) and $Q^\ominus$ is an anion.

Suitably Q is Cl, Br or I or the chemical equivalent.

The reduction reaction is suitably performed by catalytic hydrogenation.

A medium or high pressure of hydrogen is generally employed, for example 50–500 psi, more usually about 200–300 psi.

Normally the catalyst employed is Adams catalyst.

The reaction is usually performed in an alkanolic solvent such as ethanol at a non-extreme temperature, for example at ambient temperature.

In a further process aspect this invention provides a process for the preparation of a compound of the formula (II) wherein X is a group of the sub-formula (a) which comprises the reaction of a corresponding compound of the formula (XI):

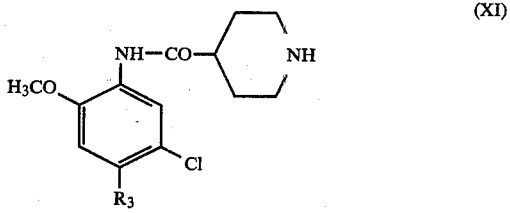

wherein $R_3$ is as defined in relation to formula (II) with a compound of the formula (XII):

$$Q_1-CHR_2-(CH_2)_n-R_1 \qquad (XII)$$

wherein $R_1$, $R_2$ and n are as defined in formula (II) and $Q_1$ is a group or atom readily displaced by a nucleophile.

Suitable values for $Q_1$ include Cl, Br, I, $OSO_2CH_3$, $OSO_2C_6H_4pCH_3$ and their chemical equivalents.

Particularly suitably the compound of the formula (XI) is a benzyl halide such as benzyl bromide or benzyl chloride.

The reaction may be carried out under conventional alkylation conditions for example in an inert solvent such as dimethylformamide in the presence of an acid acceptor such as potassium carbonate. Generally the reaction is carried out at a non-extreme temperature such as at ambient or at a slightly elevated temperature.

The following Examples illustrate the invention:

EXAMPLE 1

4-Chloro-2-(1¹-benzylpiperidine-4-carboxamido)-anisole

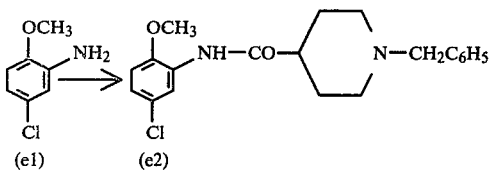

A mixture of 2-amino-4-chloro-anisole (e1) (10 g), N-benzyl-piperidine-4-carboxylic acid (13.9 g) and dicyclohexylcarbodiimide (13.15 g) in dichloromethane (250 ml) and tetrahydrofuran (250 ml) was stirred for 24 hours. The mixture was then filtered and evaporated to dryness. Ether was added to the residue and the solution again filtered and the clean solution evaporated. The residue was chromatographed on silica gel eluting with progressively graded mixtures of light petroleum, ether and ethyl acetate. 4-Chloro-2-(1¹-benzylpiperidine-4-carboxamido)anisole (e2) (12 g, 53%), m.p. 85°–87° C. was obtained, characterised further as the hydrochloride hydrate, m.p. 155°–157° C.

EXAMPLE 2

4-Chloro-2-(1¹-benzylpiperidine-4-carboxamido)-5-nitroanisole

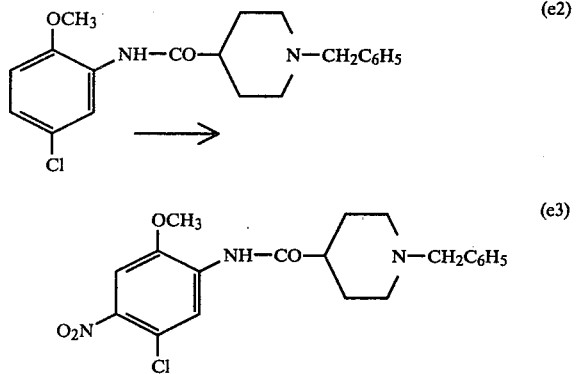

Fuming nitric acid (5 ml) was added dropwise with stirring to a solution of 4-chloro-2-(1¹-benzylpiperidine-4-carboxamido)anisole (e2) (4 g) in acetic acid (20 ml) keeping the temperature below 35° C. After 4 hours the solution was poured into water, basified (with 40% NaOH solution) and extracted with ethyl acetate. On evaporation, 4-chloro-2-(1¹-benzylpiperidine-4-carboxamido)-5-nitroanisole (e3) (3.5 g, 78%) was obtained which was later characterised as the hydrochloride m.p. 194°–5° C. (recrystallised from ethanol-ether).

Similarly prepared were (a) 4-chloro-2-[1-(2-phenyl)ethylpiperidine-4-carboxamido]-5-nitroanisole (70%), cream prisms, m.p. 131°–132°; (b) 4-chloro-2-[1-(4-chlorobenzyl)-piperidine-4-carboxamido]-5-nitroanisole (89%), brown prisms, m.p. 158°–161°; and (c) 4-chloro-2-[1-(4-methylbenzyl)-piperidine-4-carboxamido]-5-nitroanisole (65%), yellow prisms, m.p. 171°–173°.

EXAMPLE 3

5-Amino-4-chloro-2-(1¹-benzylpiperidine-4-carboxamido)-anisole

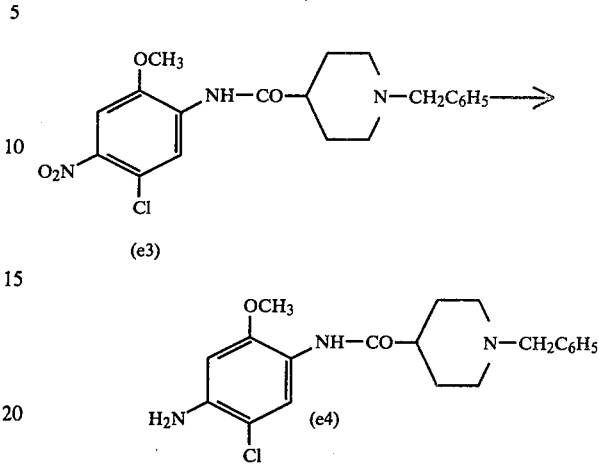

4-Chloro-2-(1¹-benzylpiperidine-4-carboxamido)-5-nitroanisole (e3) (6.44 g) was added in portions to a solution of stannous chloride dihydrate (10.82 g) in concentrated hydrochloric acid (40 ml). The mixture was stirred at 40° C. for 1 hour. The mixture was then filtered and the filtrate poured on to ice and basified. Extraction with ethyl acetate gave an oil which was chromatographed on silica gel eluting with progressively graded mixtures of light petroleum, ether and ethyl acetate. 5-Amino-4-chloro-2-(1¹-benzylpiperidine-4-carboxamido)-anisole (e4) was obtained. n.m.r. (CDCl$_3$) $\tau$ 1.72 (1H, s, 3-aromatic-$\underline{H}$), 2.48 (1H, broad s, N$\underline{H}$CO), 2.70 (5H, s, aromatic-H) 3.70 (1H, s, 6-aromatic-$\underline{H}$), 6.08 (2H, broad s, N$\underline{H}_2$), 6.20 (3H, s, OC$\underline{H}_3$), 6.48 (2H, s, N—C$\underline{H}_2$Ph), 6.88–8.38 (9H, broad multiplets, piperidine ring —$\underline{H}$).

This free base was converted to a hydrochloride (1.5 g, 23%).

EXAMPLE 4

5-Amino-4-chloro-2-(1¹-benzylpiperidine-4-carboxamido)anisole

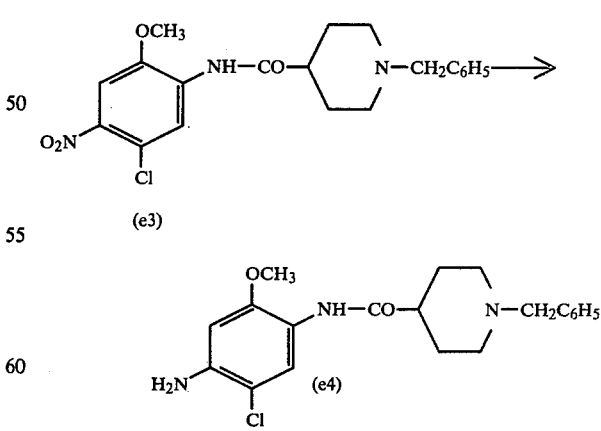

4-Chloro-2-(1¹-benzylpiperidine-4-carboxamido)-5-nitroanisole (e3) (15.4 g) was dissolved in acetic acid (150 ml) at room temperature. To this was added a solution of stannous chloride (21.7 g of anhydrous) in concentrated hydrochloric acid (50 ml). The mixture was stirred overnight at ambient temperature (~20°). The resulting clear solution was poured onto ice and the solution was rendered strongly basic with 40% NaOH solution (total volume at this stage was about 2 l). The mixture was extracted with ethyl acetate (2×150 ml). The organic phase was passed through a 2.5 cm×20 cm column of alumina. The resulting solution was evaporated to dryness to yield a buff foam (12.9 g). n.m.r. (CDCl$_3$) τ 1.78 (1H, s, 3-aromatic-$\underline{H}$), 2.50 (1H, broad, s, NH.C$\underline{O}$), 2.75 (5H, s, aromatic-$\underline{H}$), 3.76 (1H, s, 6-aromatic-$\underline{H}$), 6.09 (2H, broad, s, N$\underline{H}_2$), 6.24 (3H, s, OC$\underline{H}_3$), 6.52 (2H, s, N—C$\underline{H}_2$C$_6$H$_5$), 6.85–7.26 (2H, broad multiplet, piperidine ring $\underline{H}$), 7.57–8.49 (7H, broad multiplet, piperidine ring $\underline{H}$).

A sample of the foam (2.0 g) was recrystallised by dissolving in hot ether and adding petroleum ether (60°–80°) until the solution was opalescent and then allowed to cool. The resulting buff crystals were filtered off, washed with petrol (60°–80°) and dried to yield 1.4 g of the desired compound (e4) as buff prisms, m.p. 105°–6° C.

| Analysis | Required | Found | |
|---|---|---|---|
| C | 64.24 | 64.50 | 64.13 |
| H | 6.47 | 6.98 | 6.85 |
| N | 11.23 | 11.15 | 11.15 |
| Cl | 9.50 | 9.81 | 10.03 |

EXAMPLE 5

5-Amino-4-chloro-2-(4-N-benzyl-piperidinecarbonylamino)anisole dihydrochloride

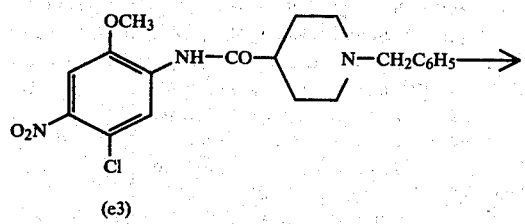

(e3)

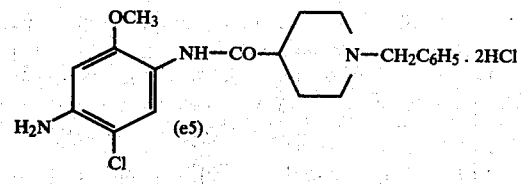

(e5)

The nitroanisole (e3) (14.7 g) was dissolved in acetic acid/concentrated hydrochloric acid (1:1, 150 ml). To this solution was added a solution of stannous chloride (20.8 g) in concentrated hydrochloric acid (50 ml). The reaction mixture was warmed to 60° C. and stirred for 1 hour at the end of which time the solution had returned to ambient temperature. The solution was poured onto ice and basified with sodium hydroxide solution (40%) to give a final volume of about 2 l. The mixture was extracted with ethyl acetate (2×150 ml) and the organic phase dried (potassium carbonate) and filtered to give a clear solution. To this solution was added excess ethereal HCl to precipitate a di-hydrochloride salt. This was dissolved in water, the resulting solution washed with ethyl acetate, basified with sodium hydroxide solution and extracted into ethyl acetate. The organic phase was dried (potassium carbonate) and the solvent evaporated to yield a brown oil (7.4 g).

The oil was dissolved in ether (100 ml) and excess of ethereal HCl was added. A solid precipitated and this was filtered off, washed with ether and transferred to a vacuum oven at 60° C. and dried thoroughly. The compound was further purified by dissolving in hot isopropanol and allowed to cool. The resulting off white solid was filtered off and dried in the vacuum oven at 60° C. to yield the desired product (e5) (5.6 g) which decomposed above 180° C.

| Analysis | Required | Found |
|---|---|---|
| C | 53.73 | 53.96 |
| H | 5.86 | 5.94 |
| N | 9.40 | 9.43 |

In a similar fashion were prepared:

(a) 5-amino-4-chloro-2-(1-(2-phenylethyl)piperidine-4-carboxamido)anisole as a brown oil (25%); n.m.r. (CDCl$_3$) τ 1.76 (1H, s, 3-aromatic-$\underline{H}$), 2.29 (1H, broad s, NHCO), 2.76 (5H, s, aromatic $\underline{H}$), 3.70 (1H, s, 6-aromatic-$\underline{H}$) 5.40–5.79 (2H, broad singlet, N$\underline{H}_2$), 6.27 (3H, s, OC$\underline{H}_3$ (6.71–8.43 (13H, broad multiplets, piperidine ring—H and NC$\underline{H}_2$CH$_2$Ph). Treatment with excess ethereal HCl gave a dihydrochloride, which decomposed at about 180°–210°.

(b) 5-amino-4-chloro-2-(1-(4-chlorobenzyl)piperidine-4-carboxamido)anisole as a brown oil (46%). n.m.r. (CDCl$_3$), τ 1.78 (1H, s, 3-aromatic-$\underline{H}$), 2.48 (1H, broad s, NHCO), 2.77 (4H, s, aromatic H), 3.73 (1H, s, 6-aromatic-H), 6.02 (2H, broad s, N$\underline{H}_2$), 6.22 (3H, s, OC$\underline{H}_3$), 6.55 (2H, s, N—C$\underline{H}_2$—Ar), 6.35–7.28 (2H, broad multiplet, piperidine ring $\underline{H}$), 7.63–8.22 (7H, broad multiplet, piperidine ring $\underline{H}$). The compound was converted to a di-hydrochloride as described above. to yield a dihydrochloride, which decomposed at about 180°–210°.

(c) 5-amino-4-chloro-2-(1-(4-methylphenyl)piperidine-4-carboxamido)anisole as a brown oil, (72%); n.m.r. (CDCl$_3$) τ 1.74 (1H, s, 3-aromatic-$\underline{H}$) 2.48 (1H, broad s, N$\underline{H}$CO), 2.65–3.01 (4H, broad multiplet, aromatic-$\underline{H}$), 3.70 (1H, s, 6-aromatic-$\underline{H}$) 5.38 (2H, broad s, N$\underline{H}_2$), 6.19 (3H, s, OC$\underline{H}_3$) 6.43 (2H, s, NCH$_2$Ar), 6.76–7.15 (2H, broad multiplet, piperidine-$\underline{H}$), 7.54–8.20 (10H, broad multiplet, piperidine-$\underline{H}$ and aromatic CH$_3$). The compound was converted to a dihydrochloride as described above which decomposed at about 180°–210°.

(d) 5-amino-4-chloro-2-(1-(4-methoxyphenyl)piperidine-4-carboxamido)anisole as a brown foam (75%); n.m.r. (CDCl$_3$), τ 1.80 (1H, s, aromatic $\underline{H}$), 2.49 (1H, broad, N$\underline{H}$CO), 2.66–3.31 (4H, complex multiplet, aromatic $\underline{H}$), 3.79 (1H, s, 6-aromatic $\underline{H}$), 6.09 (2H, broad s, N$\underline{H}_2$), 6.25 (6H, s, OC$\underline{H}_3$) 6.60 (2H, s, NC$\underline{H}_2$Ar), 6.84–7.26 (2H, broad multiplet, piperidine $\underline{H}$), 7.59–8.31 (7H, broad multiplet, piperidine $\underline{H}$). The compound was converted to a dihydrochloride, as described above which decomposes at about 180°–210°.

EXAMPLE 6

N-(4-Acetylamino-5-chloro-2-methoxyphenyl)-4-benzylpiperazine-1-carboxamide

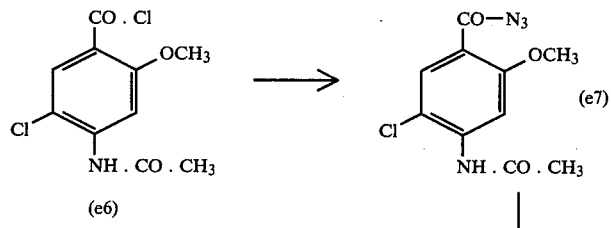

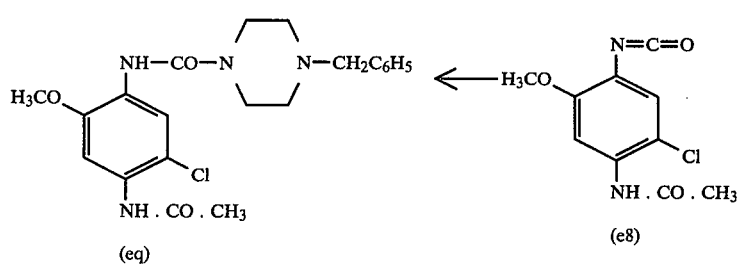

An acetone solution of 4-acetylamino-5-chloro-2-methoxy-benzoyl chloride (e6) (2.0 g) was added to a stirred aqueous solution of sodium azide (2.0 g) and the suspension stirred at room temperature for 30 minutes. Extraction with ethyl acetate gave 4-acetylamino-5-chloro-2-methoxy-benzoyl azide (e7) (4.3 g) as a white crystalline solid on trituration under petrol, m.p. 135°–140°. [I.R.$\nu$ (N$_3$)=2140 cm$^{-1}$ and $\nu$ (C=O)=1645, 1705 cm$^{-1}$].

A solution of the 4-acetylamino-5-chloro-2-methoxy benzoyl azide (e7) (1.35 g) in dry toluene (30 ml) was heated to 90° for 30 minutes with stirring under dry nitrogen until the evolution of nitrogen ceased. A dichloromethane solution of 1-benzylpiperazine (0.9 g) was then added to the cooled suspension of the isocyanate (e8) and the resulting solution stirred at room temperature for 1 hour. The reaction mixture was then poured into petrol (200 ml) and the precipitated solid filtered off. Recrystallisation from toluene give the N-(4-acetylamino-5-chloro-2-methoxyphenyl)-4-benzylpiperazine-1-carboxamide (e9) (1.4 g) m.p. 174°.

EXAMPLE 7

N-(4-Amino-5-chloro-2-methoxyphenyl)-4-benzylpiperazine-1-carboxamide

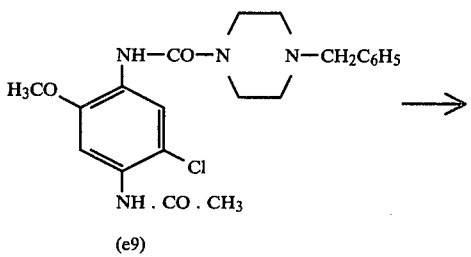

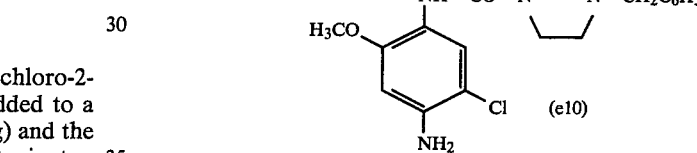

A solution of N-(4-acetylamino-5-chloro-2-methoxyphenyl)-4-benzylpiperazine-1-carboxamide (e9) (1.4 g) in ethanol (20 ml) was refluxed for 1 hour with an aqueous (4 ml) solution of potassium hydroxide (0.6 g). The solvent was removed by evaporation and the residue extracted with ethyl acetate. Chromatography of the solution (on alumina with 5% water, in chloroform) followed by evaporation of the solvent yielded N-(4-amino-5-chloro-2-methoxyphenyl)-4-benzylpiperazine-1-carboxamide (e10).

n.m.r. (CDCl$_3$) $\tau$ 2.00 (1H, s, 3-aromatic-$\underline{H}$), 2.70 (5H, s, aromatic-$\underline{H}$), 3.30 (1H, broad s, N$\underline{H}$CO), 3.73 (1H, s, 6-aromatic-$\underline{H}$), 6.0–6.3 (2H, broad s, N$\underline{H}_2$), 6.24 (3H, s, OCH$_3$), 6.4–6.7 (4H, broad multiplets-piperazine ring —$\underline{H}$), 7.4–7.7 (4H, broad multiplets-piperazine ring —$\underline{H}$).

The free base was further characterised by conversion to a hydrochloride (30% overall), m.p. 168° (dec).

EXAMPLE 8

N-(4-Acetylamino-5-chloro-2-methoxyphenyl)-N$^1$-(1-benzyl-4-piperidino)urea

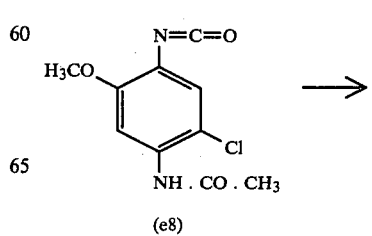

-continued

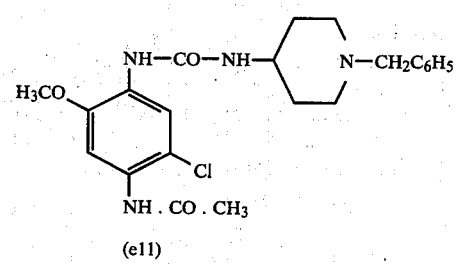

(e11)

4-Acetylamino-5-chloro-2-methoxy-benzoyl azide (e7) (2.2 g) was rearranged to the isocyanate (e8) as described in Example 6 and then reacted with 4-amino-1-benzylpiperidine (1.56 g) by the method of Example 6 to yield N-(4-acetylamino-5-chloro-2-methoxyphenyl)-$N^1$-(1-benzyl-4-piperidine)urea (e11) as a pale yellow solid (2.3 g), m.p. >230° (dec).

EXAMPLE 9

N-(4-Amino-5-chloro-2-methoxyphenyl)-$N^1$-1-benzyl-4-piperidine)urea

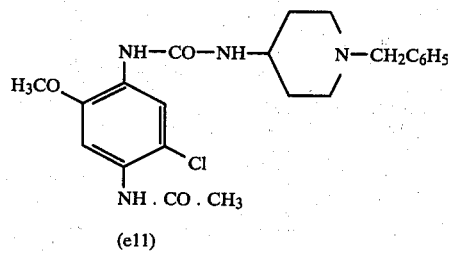

(e11)

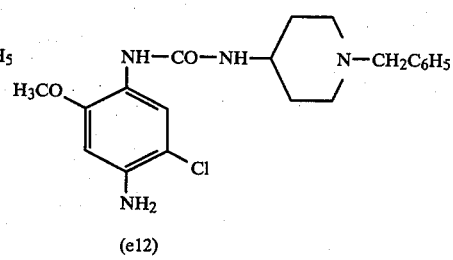

(e12)

N-(4-Acetylamino-5-chloro-2-methoxyphenyl)-$N^1$-(1-benzyl-4-piperidine)urea (e11) was hydrolysed by the method of Example 7 to yield N-(4-amino-5-chloro-2-methoxyphenyl)-$N^1$-(benzyl-4-piperidine)urea (e12) as a light grey solid (1.6 g) m.p. 150°–153° C.

EXAMPLE 10

2-(1-Benzylpiperidine-4-carboxamido)-4-chloroanisole

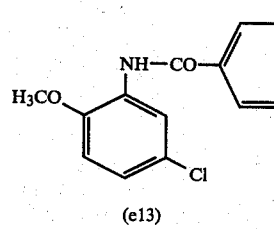

(e13)

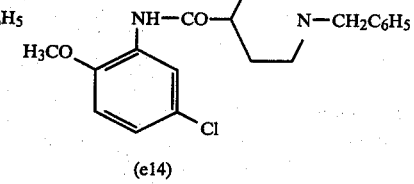

(e14)

2-(1-Benzylpyridinium-4-carboxamido)-4-chloroanisole chloride (e13) (26.8 g) was hydrogenated over Adams catalyst (0.8 g) at 250 psi in ethanol (500 ml) at room temperature. When hydrogen uptake ceased, the solution was filtered, evaporated to dryness and the residue shaken with a mixture of ethyl acetate and sodium carbonate solution. The organic layer was dried (sodium carbonate), filtered and evaporated and the residue purified by chromatography on silica gel, eluting with graded mixtures of light petroleum and ethyl acetate to yield after evaporation 2-(1-benzyl-piperidine-4-carboxamido)-4-chloroanisole (e14) (14.1 g), m.p. 84°–87° C.

[The starting material (e13) was prepared as follows: Pyridine-4-carboxylic acid (22.9 g) was dissolved in hexamethylphosphoramide (150 ml), the solution cooled in an ice bath and thionyl chloride (14.2 ml) added. After 30 minutes 2-amino-4-chloroanisole (29.4 g) in hexamethylphosphoramide (50 ml) was added and the mixture stirred overnight. The solution was poured into water and basified. 4-Chloro-2-(pyridine-4-carboxamido)anisole was filtered off, washed well with water, dried, and crystallised from ethyl acetate-light petroleum as buff prisms (38.5 g), m.p. 147°–149°.

A solution of 4-chloro-2-(pyridine-4-carboxamido)anisole (25 g) and benzyl chloride (12 ml) in dimethylformamide (250 ml) was heated at 110° for 4 hours. The solvent was removed and the residue boiled with ethyl acetate for a few minutes, then filtered off and washed well with ethyl acetate. The benzyl-pyridinium chloride (e13) was obtained as a yellow powder (30.0 g).]

EXAMPLE 11

4-Chloro-2-(1-[4-chlorobenzyl]-piperidine-4-carboxamido)anisole

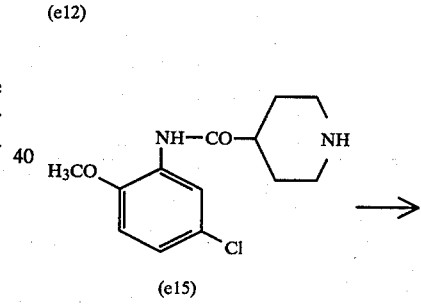

(e15)

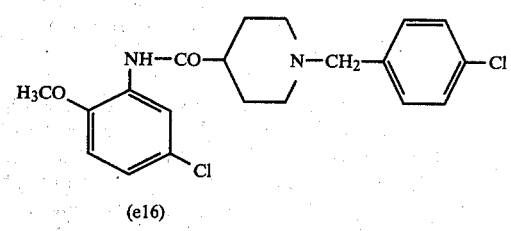

(e16)

4-Chloro-1-(4-piperidine carboxamide)anisole (e15) (5 g), 4-chlorobenzyl chloride (3.6 g) and potassium carbonate (3.1 g) were stirred together in dimethylformamide (150 ml) at room temperature for 17 hours. The solvent was removed and the residue taken up in a mixture of chloroform and water. The organic layer was dried ($K_2CO_3$), filtered and evaporated to dryness to yield 4-chloro-2-(1-[4-chlorobenzyl]-piperidine-4-carboxamido) anisole (e16). This was converted to the hydrochloride salt which was recrystallised from ethanol-ethyl acetate (7.4 g), m.p. 239°–243° C.

The starting material (e15) was prepared as follows: 4-Chloro-2-(4-pyridinecarboxamido)anisole hydrochloride (from E14) (10 g) was hydrogenated over Adams' catalyst (0.25 g) at 300 psi in ethanol (250 ml) at 70° for 6 hours. The residue obtained after filtration and evaporation was taken up in a mixture of ethyl acetate and aqueous sodium carbonate, the organic layer was dried ($Na_2CO_3$) filtered and evaporated to give 4-chloro-2-(piperidine-4-carboxamido)anisole as a cream-coloured powder (7.4 g). (A portion was recrystallised from ethyl acetate to give white prisms, m.p. 124°–126°.)

EXAMPLE 12

4-Chloro-2-(1-(4-methoxybenzyl)-piperidine-4-carboxamido)-5-nitroanisole

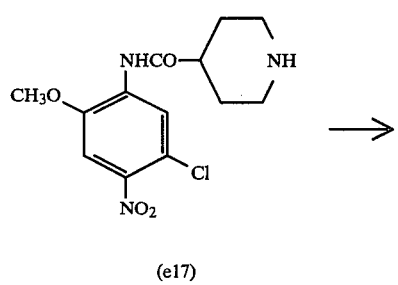

(e17)

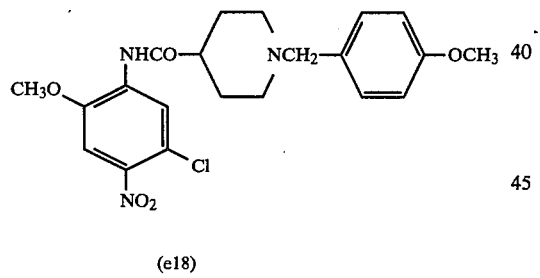

(e18)

4-Chloro-5-nitro-2-(piperidine-4-carboxamido)anisole (e17) (3.14 g), 4-methoxybenzyl chloride (1.57 g) and potassium carbonate (1.4 g) were stirred together in dimethylformamide (50 ml) for 16 h. The solvent was removed at the pump and ethyl acetate (200 ml) and sodium hydroxide (10%, 200 ml) were added to the residue. The ethyl acetate extract was eluted through alumina and the filtrate evaporated to yield a brown residue, which crystallised as brown prisms from ethyl acetate-petrol ether (b.p. 60°–80°), (2.96 g, 68%) m.p. 138°–142°.

Similarly prepared was 4-chloro-2-[1-(4-methylbenzyl)piperidine-4-carboxamido]anisole hydrochloride monohydrate, white prisms (71%), m.p. 222°–225°.

The starting material (e17) was prepared as follows:
4-Chloro-2-(piperidine-4-carboxamido)anisole (10.4 g) was dissolved in a mixture of acetic acid (100 ml) and concentrated sulphuric acid (5 ml). Fuming nitric acid (2.1 ml) was added dropwise, keeping the temperature below 30°. The solution was stirred at room temperature for 2 hr, poured onto crushed ice (ca 500 ml) and basified with 40% sodium hydroxide. The mixture was extracted with ethyl acetate (2×250 ml), the extracts dried ($K_2CO_3$) and solvent removed at the pump. The brown residue was crystallised from ethyl acetate and petroleum ether (b.p. 60°–80°), giving 4-chloro-5-nitro-2-(piperidine-4-carboxamido)anisole as brown plates (e17) (9.9 g, 82%), m.p. 167°–170°.

EXAMPLE 13

Compositions (a) Tablets of the following composition may be prepared:

| | |
|---|---|
| 5-Amino-4-chloro-2-(1-benzylpiperidine)-4-carboxamido)anisole dihydrochloride | 25 mg |
| Microcrystalline cellulose | 123 mg |
| Magnesium stearate | 2 mg |

(A similar tablet may be produced containing an equivalent amount of the mono-hydrochloride.)

(b) Hard gelatin capsules may be prepared containing the following:

| | |
|---|---|
| 5-Amino-4-chloro-2-(1-benzylpiperidine-4-carboxamido)anisole mono-hydrochloride | 25 mg |
| Lactose | 70 mg |
| Sodium lauryl sulphate | 5 mg |

(A similar capsule formulation may be produced containing an equivalent amount of the di-hydrochloride.)

DESCRIPTION 1

Pharmacology a. The compound of Example 3 was active on the amphetamine stereotypy test in rats [based on Janssen et al, Arzenimittelforsch, 15, 104–117, (1966)] where it had an $ED_{50}$ of 0.2 mg/kg when administered sub-cutaneously. On the anti-catepressan test [based on Costal et al, Europ. J. Pharmacol., 18, 83–94 (1972)] the compound of this Example had an $ED_{50}$ of 5 mg/kg per oral. The $LD_{50}$ of the compound of Example 3 is about 500 mg/kg per oral in the mouse.

b. 5-Amino-4-chloro-2-(1-benzylpiperidine-4-carboxamido) anisole and its salts have anti-psychotic or neuroleptic activity as judged by the induction of amphetamine induced stereotypy test. This compound and its salts are of particular interest because they show a weaker propensity to induce catalepsy (an indicator of potential extrapyramidol side effects) relative to its anti-stereotypy activity than such clinically used compounds as haloperidol or chlorpromazine. These results are shown in the following Table 1.

TABLE 1

| Antagonism of compound | $ED_{50}$ (mg/kg S.C.) | | |
|---|---|---|---|
| | Induction of amphetamine induced stereotypy | Induction of catalepsy | Ratio catalepsy anti-sterotypy |
| 5-Amino-4-chloro-2 (1-benzylpiperidine-4-carboxamido) | 0.2 | 6.0 | 30 |

TABLE 1-continued

| Antagonism of compound | ED$_{50}$ (mg/kg S.C.) | | |
|---|---|---|---|
| | Induction of amphetamine induced stereotypy | Induction of catalepsy | Ratio catalepsy anti-sterotypy |
| anisole or its mono- or di-hydrochloride | | | |
| Haloperidol | 0.05 | 0.3 | 6 |
| Chlorpromazine | 1.0 | 3.0 | 3 |

What we claim is:

1. A compound of the formula:

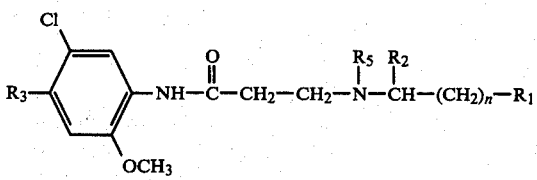

and the N-oxides and the pharmaceutically acceptable salts thereof wherein $R_1$ is phenyl unsubstituted or substituted by fluoro chloro, bromo, alkyl of 1 to 3 carbon atoms or alkoxy of 1 to 3 carbon atoms;

$R_2$ is hydrogen or alkyl of 1 to 4 carbon atoms;

$R_3$ is hydrogen, nitro, amino,

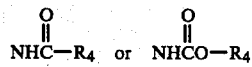

in which $R_4$ is alkyl of 1 to 4 carbon atoms unsubstituted or substituted with up to three chlorine atoms or with three fluorine atoms on the same carbon atoms;

$R_5$ is alkyl of 1 to 4 carbon atoms n has a value of 0, 1 or 2.

2. A compound as claimed in claim 1 wherein $R_1$ is phenyl, p-chlorophenyl, p-methylphenyl or p-methoxyphenyl.

3. A compound as claimed in claim 1 wherein $R_1$ is phenyl.

4. A compound as claimed in claim 1 wherein $R_2$ is hydrogen, methyl, ethyl, n-propyl or n-butyl.

5. A compound as claimed in claim 1 wherein $R_2$ is hydrogen or methyl.

6. A compound as claimed in claim 1 wherein $R_2$ is hydrogen.

7. A compound as claimed in claim 1 wherein n is 0.

8. A compound as claimed in claim 1 wherein $R_2$ is hydrogen, n is 0 and $R_1$ is phenyl.

9. A compound as claimed in claim 1 wherein $R_3$ is hydrogen.

10. A compound as claimed in claim 1 wherein $R_3$ is nitro.

11. A compound as claimed in claim 1 wherein $R_3$ is amino, NHCOR, or NHCO$_2$R$_4$ where R$_4$ is alkyl of 1 to 4 carbon atoms.

12. A compound as claimed in claim 1 wherein $R_3$ is amino, acetylamino, propionylamino, methoxycarbonylamino or ethoxycarbonylamino.

13. A compound as claimed in claim 1 wherein $R_3$ is amino or acetylamino.

14. A compound as claimed in claim 1 wherein $R_3$ is amino.

15. A compound of the formula:

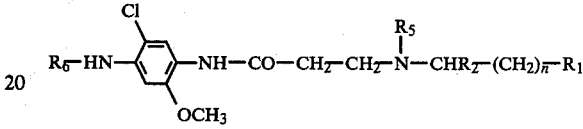

or a pharmaceutically acceptable salt thereof wherein $R_1$ is phenyl unsubstituted or substituted with fluoro, chloro, bromo, alkyl of 1 to 3 carbon atoms or alkoxy of 1 to 3 carbon atoms;

$R_2$ is hydrogen or alkyl of 1 to 4 carbon atoms;

n is 0, 1 or 2;

$R_5$ is alkyl of 1 to 4 carbon atoms; and $R_6$ is hydrogen, COR$_4$ or CO$_2$R$_4$ wherein R$_4$ is alkyl of 1 to 4 carbon atoms unsubstituted or substituted with one, two or three chlorine atoms or with three fluorine atoms on the same carbon atom.

16. A compound as claimed in claim 15 wherein $R_6$ is hydrogen.

17. A compound as claimed in claim 16 wherein $R_1$ is phenyl, p-chlorophenyl, p-methoxyphenyl or p-methylphenyl.

18. A compound as claimed in claim 16 wherein $R_1$ is phenyl.

19. A compound as claimed in claim 16 wherein $R_2$ is hydrogen, methyl, ethyl, n-propyl or n-butyl.

20. A compound as claimed in claim 16 wherein $R_2$ is hydrogen or methyl.

21. A compound as claimed in claim 16 wherein $R_2$ is hydrogen.

22. A compound as claimed in claim 16 wherein n is 0.

23. A compound as claimed in claim 1 in the form of the free base.

24. A compound as claimed in claim 1 in the form of a pharmaceutically acceptable acid addition salt.

25. A compound as claimed in claim 16 in the form of a mono-acid addition salt.

* * * * *